United States Patent
Matsudate et al.

(10) Patent No.: US 9,677,955 B2
(45) Date of Patent: Jun. 13, 2017

(54) CONTACT FORCE SENSOR

(71) Applicant: SEMITEC CORPORATION, Tokyo (JP)

(72) Inventors: Tadashi Matsudate, Tokyo (JP); Shuji Inamura, Tokyo (JP)

(73) Assignee: SEMITEC CORPORATION, Tokyo (JP)

( * ) Notice: Subject to any disclaimer, the term of this patent is extended or adjusted under 35 U.S.C. 154(b) by 168 days.

(21) Appl. No.: 14/648,260

(22) PCT Filed: Mar. 18, 2014

(86) PCT No.: PCT/JP2014/057304
§ 371 (c)(1),
(2) Date: May 29, 2015

(87) PCT Pub. No.: WO2014/156823
PCT Pub. Date: Oct. 2, 2014

(65) Prior Publication Data
US 2015/0300895 A1    Oct. 22, 2015

(30) Foreign Application Priority Data
Mar. 27, 2013    (JP) .................... 2013-067294

(51) Int. Cl.
*G01L 1/18*    (2006.01)
*A61B 18/14*    (2006.01)
(Continued)

(52) U.S. Cl.
CPC ............ *G01L 1/18* (2013.01); *A61B 18/1492* (2013.01); *G01L 5/162* (2013.01);
(Continued)

(58) Field of Classification Search
CPC ....... G01L 1/18; G01L 5/162; A61B 18/1492; A61B 2018/00351; A61B 2018/00773;
(Continued)

(56) References Cited

U.S. PATENT DOCUMENTS

| | | | | |
|---|---|---|---|---|
| 4,429,413 A | * | 1/1984 | Edwards | A61B 5/1172 257/E27.006 |
| 6,347,555 B1 | * | 2/2002 | Namerikawa | G01L 1/18 73/760 |
| 8,631,711 B2 | * | 1/2014 | Huffman | G01L 9/0013 73/760 |
| 2008/0047366 A1 | * | 2/2008 | Kuriyama | G01L 1/2268 73/862.627 |
| 2011/0314923 A1 | * | 12/2011 | Hou | G01L 1/18 73/727 |

(Continued)

FOREIGN PATENT DOCUMENTS

| | | |
|---|---|---|
| CN | 102192805 | 9/2011 |
| CN | 202720078 | 2/2013 |
| JP | 10-289780 | 10/1998 |
| JP | 11-333765 | 12/1999 |
| JP | 2003-083820 | 3/2003 |
| JP | 2004-069405 | 3/2004 |
| JP | 2004-163166 | 6/2004 |
| JP | 2008-032511 | 2/2008 |

(Continued)

OTHER PUBLICATIONS

"International Search Report (Form PCT/ISA/210)", mailed on Apr. 22, 2014, with English translation thereof, pp. 1-4, in which six of the listed references (JP2004-069405, JP11-333765, JP2004-163166, JP2003-083820, JP10-289780 and JP2008-032511) were cited.

(Continued)

*Primary Examiner* — David Bolduc
(74) *Attorney, Agent, or Firm* — Jianq Chyun IP Office

(57) ABSTRACT

Provided is a contact force sensor of high sensitivity and high accuracy. This contact force sensor is fabricated by machining of a silicon semiconductor material. The contact force sensor is provided with a sensor configuration having a base part, and a contact force transmission part formed in a direction orthogonal to this base part. A stress-electricity conversion element for converting displacement of the contact force transmission part to an electrical signal, formed in the base part of the sensor configuration, is also provided.

10 Claims, 7 Drawing Sheets

(51) Int. Cl.
  *G01L 5/16* (2006.01)
  *A61B 18/00* (2006.01)
  *A61B 90/00* (2016.01)

(52) U.S. Cl.
  CPC ............... *A61B 2018/00351* (2013.01); *A61B 2018/00577* (2013.01); *A61B 2018/00595* (2013.01); *A61B 2018/00773* (2013.01); *A61B 2090/065* (2016.02); *A61B 2090/376* (2016.02)

(58) Field of Classification Search
  CPC   A61B 2018/00577; A61B 2018/00595; A61B 2090/065; A61B 2090/376
  See application file for complete search history.

(56) References Cited

U.S. PATENT DOCUMENTS

2015/0128725 A1\* 5/2015 Ichige ................... G01L 1/2231
                                                                                73/862.045

FOREIGN PATENT DOCUMENTS

| | | |
|---|---|---|
| JP | 2011-507605 | 3/2011 |
| JP | 2011-147783 | 8/2011 |

OTHER PUBLICATIONS

"First Office Action of China Counterpart Application" with English translation thereof, issued on Oct. 31, 2016, p. 1-p. 15.

\* cited by examiner

CONTACT FORCE SENSOR

CROSS-REFERENCE TO RELATED APPLICATION

This application is a 371 application of an international PCT application serial no. PCT/JP2014/057304, filed on Mar. 18, 2014, which claims the priority benefit of Japan application no. 2013-067294, filed on Mar. 27, 2013. The entirety of each of the above-mentioned patent applications is hereby incorporated by reference herein and made a part of this specification.

BACKGROUND OF THE INVENTION

Field of the Invention

The invention relates to a contact force sensor for use in an ablation catheter, etc.

Description of Related Art

It is known that an ablation treatment is to percutaneously insert a catheter into a target site in the heart and apply a high frequency current through an electrode disposed on the tip of the catheter to selectively cauterize the abnormal site, so as to treat atrial arrhythmia, etc.

The ablation treatment cures arrhythmia by cauterizing a conduction path of an abnormal electrical signal that causes arrhythmia in the heart to block the conduction path.

To perform the ablation treatment, an ablation catheter is used, in which an electrode that allows passage of high frequency electricity is disposed on the tip of the ablation catheter for cauterizing the conduction path of the abnormal electrical signal in the heart (see Patent Literature 1, for example).

During the ablation treatment that uses such an ablation catheter, the electrode of the ablation catheter is placed in contact with the abnormal site on the inner wall of the heart and then a high frequency current is applied to cauterize the abnormal site.

However, if the contact force the electrode applies on the abnormal site on the inner wall of the heart is not strong enough, the abnormal electrical conduction path may not be cauterized sufficiently; on the other hand, an excessive contact force may penetrate the inner wall of the heart and cause a complication, such as cardiac tamponade.

For this reason, a catheter with a contact force sensor for sensing the contact force of the electrode on the tip has been proposed (see Patent Literature 2).

PRIOR ART LITERATURE

Patent Literature

Patent Literature 1: Japanese Patent Publication No. 2011-507605
Patent Literature 2: Japanese Patent Publication No. 2011-147783

SUMMARY OF THE INVENTION

Problem to be Solved

Regarding the catheter provided with the aforementioned contact force sensor, the contact force sensor is made of a metallic sensor configuration that has a strain gauge attached thereto by an adhesive. Since it is difficult to directly apply the contact force to the strain gauge, the contact force sensor has the problem of low sensitivity and low accuracy.

In view of the above issue, the invention provides a contact force sensor of high sensitivity and high accuracy.

As one aspect of the present invention, the contact force sensor is fabricated by machining a semiconductor material, and the contact force sensor includes: a first sensor configuration including a base part, a contact force transmission part formed in a direction orthogonal to the base part, and a stress-electricity conversion element formed on a rear side of a forming surface of the base part, wherein the contact force transmission part is formed on the forming surface of the base part and the stress-electricity conversion element converts a displacement of the contact force transmission part to an electrical signal; and a second sensor configuration including a coupling surface coupled to a rear side of the first sensor configuration, and a stress-electricity conversion element being formed on the coupling surface, wherein the rear side of the first sensor configuration and the coupling surface of the second sensor configuration are coupled to sandwich a connection part of a lead wire connected to the stress-electricity conversion element and are arranged such that the stress-electricity conversion elements formed respectively face each other.

The contact force sensor has the stress-electricity conversion element, such as a piezoresistive element formed integrally with the base part. Thus, a useful contact force sensor of high sensitivity and high accuracy is provided.

As one aspect of the present invention, in the contact force sensor, the base part of the first sensor configuration includes a ring-shaped part and a plurality of arm parts extending from an inner side of the ring-shaped part to a central part, and the contact force transmission part is connected with the plurality of arm parts at the central part of the ring-shaped part.

As one aspect of the present invention, in the contact force sensor, at least one stress-electricity conversion element is formed respectively in the plurality of arm parts. Therefore, the contact force can be sensed three-dimensionally.

As one aspect of the present invention, in the contact force sensor, a wiring pattern connecting a plurality of the stress-electricity conversion elements together is formed in the base part of the first sensor configuration.

Therefore, lead wires can be reduced to simplify the wiring relation.

As one aspect of the present invention, in the contact force sensor, an insulating layer is interposed between the base part and the contact force transmission part.

Thus, it is possible to ensure the insulation between the base part and the contact force transmission part.

As one aspect of the present invention, in the contact force sensor, the semiconductor material is a SOI substrate.

Generally, the SOI substrate is a substrate prepared by forming a silicon oxide film, i.e. an insulating layer, on a silicon wafer.

As one aspect of the present invention, in the contact force sensor, the connection part of the lead wire connected to the stress-electricity conversion element is coupled by soldering and sandwiched between the first sensor configuration and the second sensor configuration.

According to the invention, the coupling strength of the connection part of the lead wire coupled by soldering can be improved.

As one aspect of the present invention, in the contact force sensor, the coupling surface of the second sensor configuration is formed into a shape suitable to a shape of the rear side of the first sensor configuration.

As one aspect of the present invention, in the contact force sensor, the stress-electricity conversion element forms a bridge circuit, and all the stress-electricity conversion elements that form the bridge circuit detect the displacement of the contact force transmission part.

Effects of the Invention

The invention provides a contact force sensor of high sensitivity and high accuracy.

DESCRIPTION OF THE EMBODIMENTS

Figure 1:
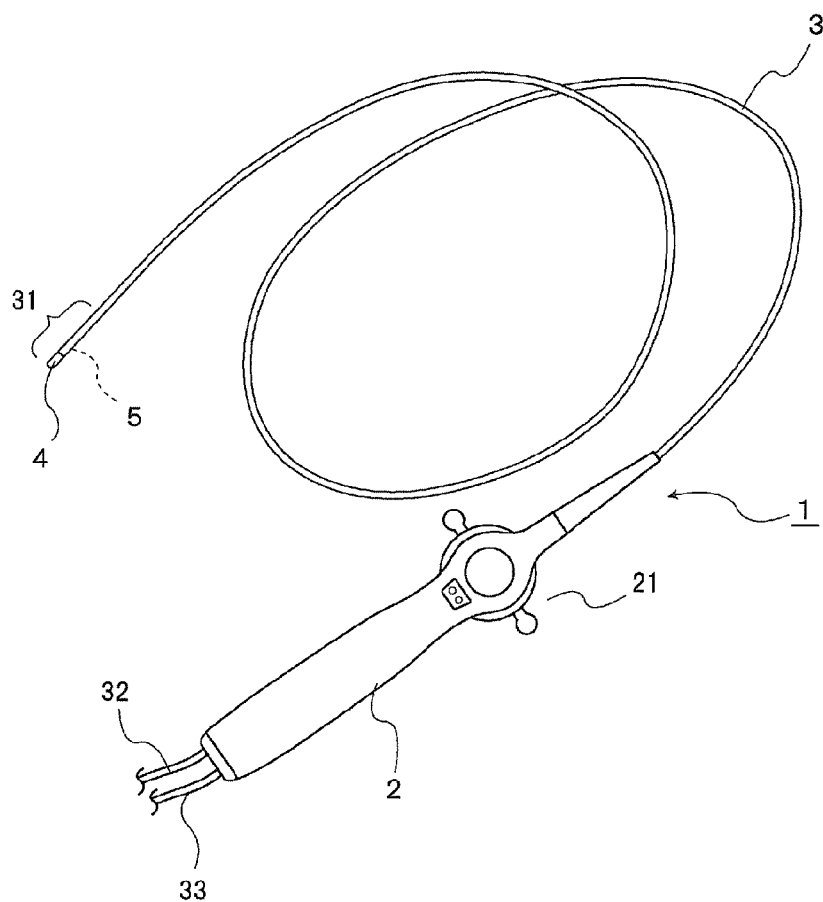
FIG. 1 is a plan view of a catheter using the contact force sensor of an embodiment of the invention.
Figure 2:
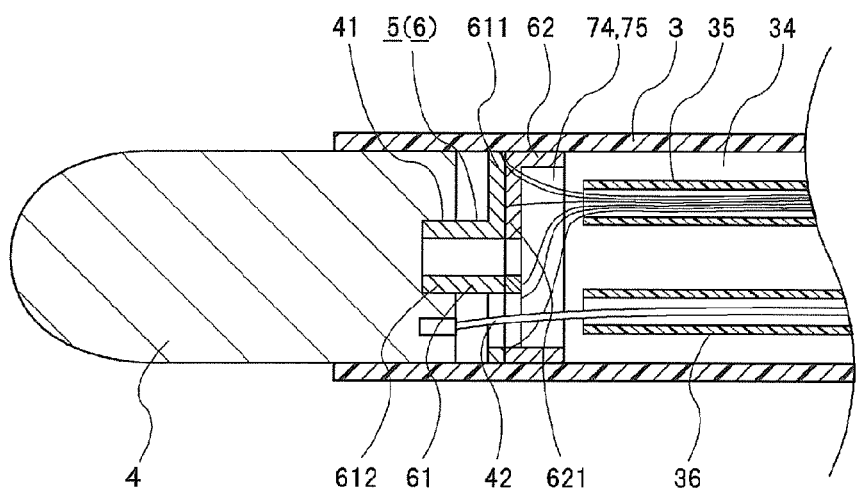
FIG. 2 is a schematic cross-sectional view of a tip part of the catheter.
Figure 3:
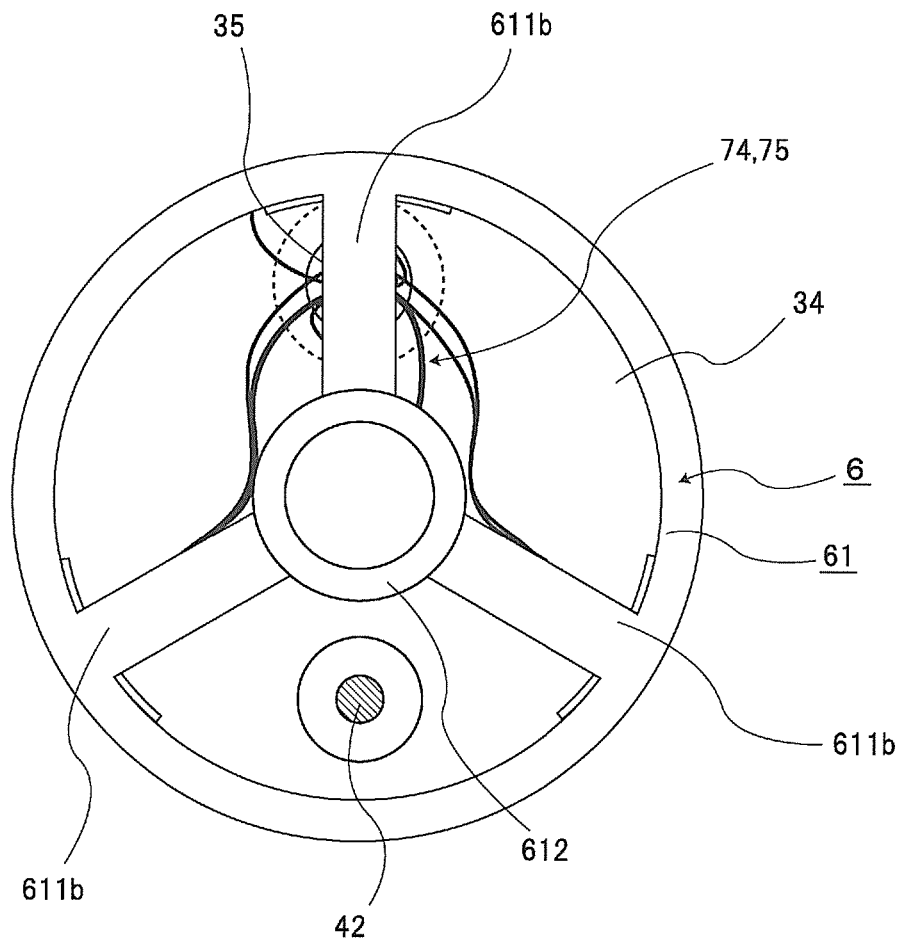
FIG. 3 is a plan view showing wiring of a lead wire derived from the contact force sensor.
Figure 4:
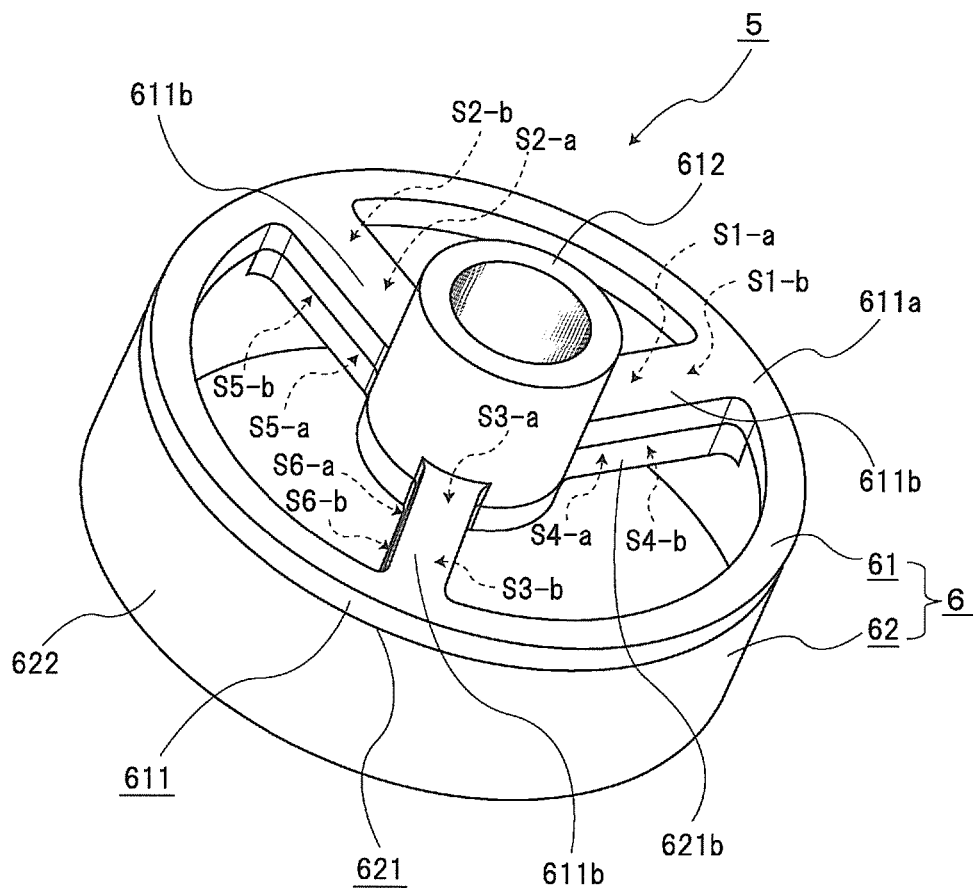
FIG. 4 is a perspective view of the contact force sensor.
Figure 5:
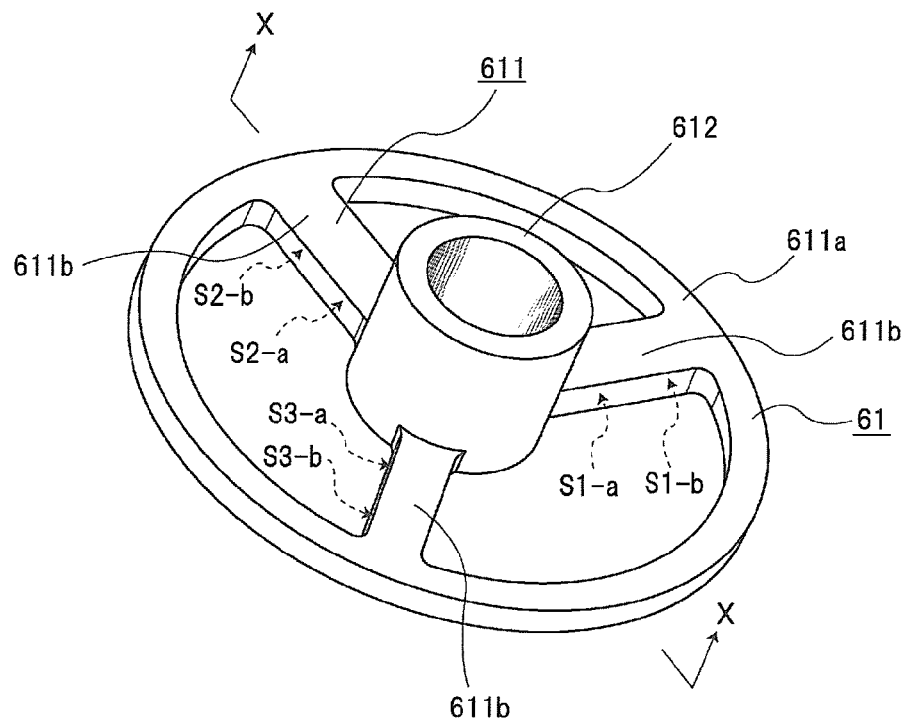
FIG. 5 is an exploded perspective view of the contact force sensor.
Figure 5:
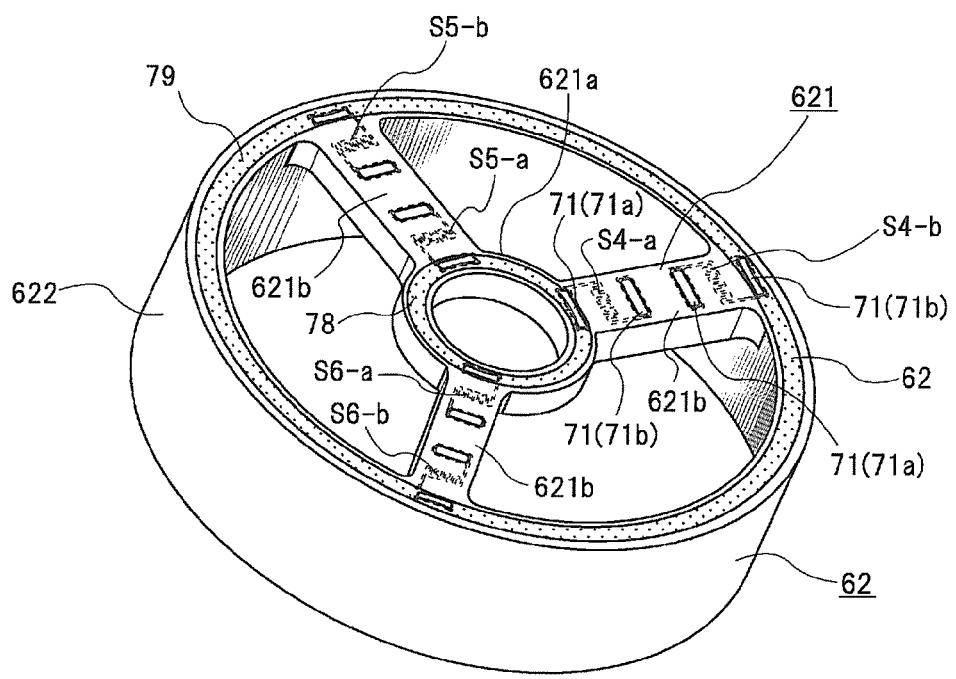
Figure 6:
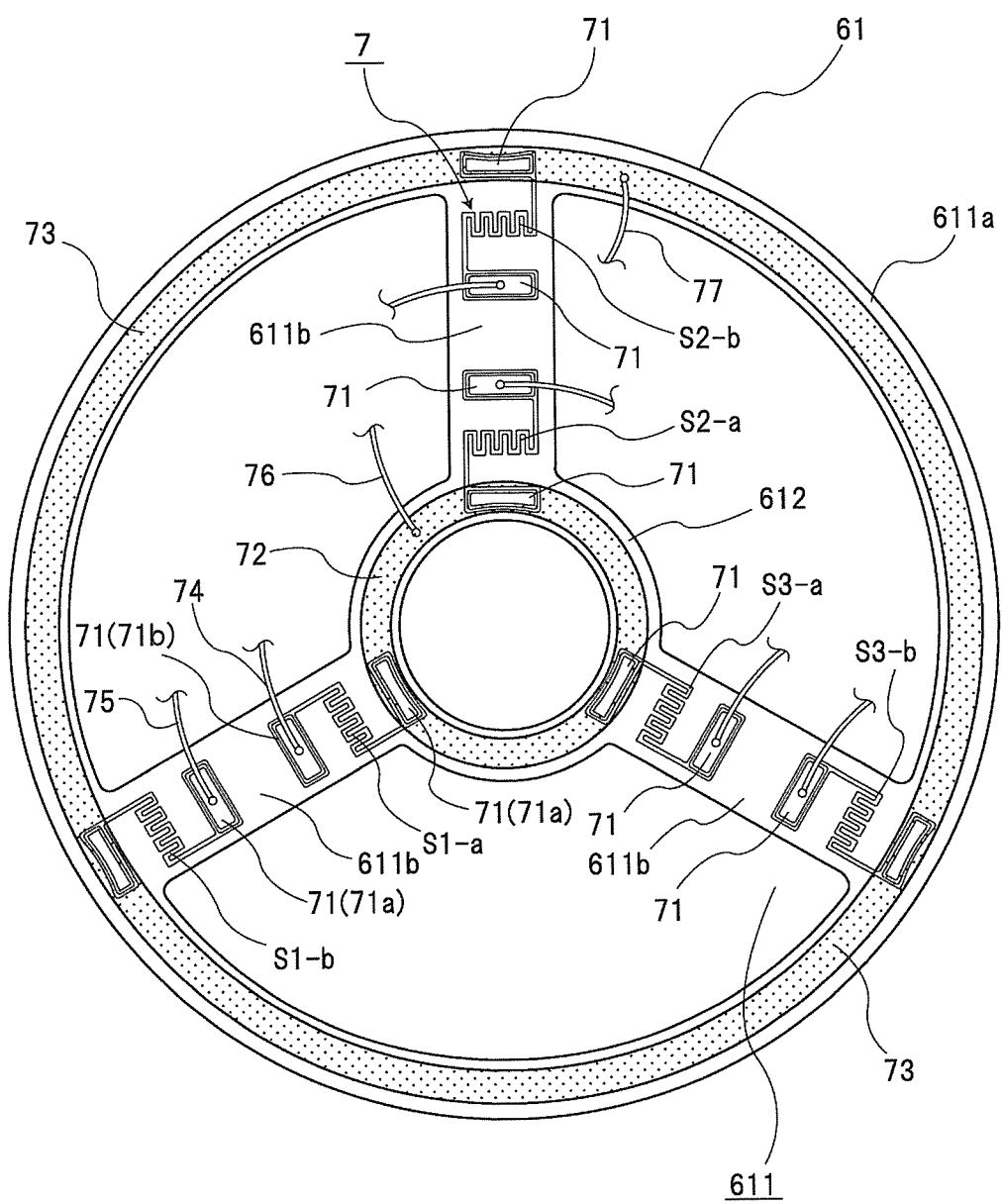
FIG. 6 is a bottom view showing configuration of a stress-electricity conversion element in the contact force sensor.
Figure 7:
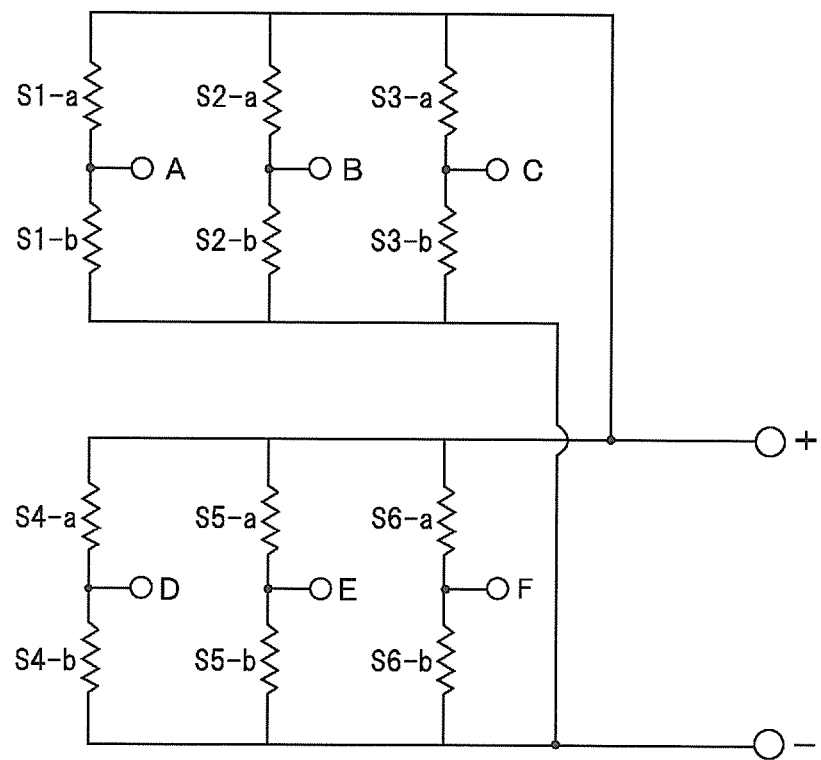
FIG. 7 is a bridge circuit diagram showing connection of the stress-electricity conversion element.

Hereinafter, a contact force sensor relating to the embodiments of the invention is described with reference to FIG. 1 through FIGS. 8(a)-8(e). FIG. 1 is a plan view of a catheter using the contact force sensor. FIG. 2 is a cross-sectional view schematically illustrating a tip part of the catheter. FIG. 3 is a plan view showing wiring of a lead wire derived from the contact force sensor. FIG. 4 is a perspective view of the contact force sensor, and FIG. 5 is an exploded perspective view of the contact force sensor. FIG. 6 is a bottom view showing configuration of a stress-electricity conversion element (piezoresistive element) in the contact force sensor. FIG. 7 is a bridge circuit diagram showing connection of the stress-electricity conversion element. FIG. 8(a) to FIG. 8(e) include cross-sectional views outlining production processes of the contact force sensor and illustrates the cross section along the line X-X of FIG. 5. In the respective figure, the scale of the component is modified to an appropriate size to help understand the component.

As shown in FIG. 1, the catheter 1 is an ablation catheter and includes a control handle 2 and a shaft 3 derived from one end of the control handle 2. The control handle 2 is provided with a deflection member 21, and a tip electrode 4 is disposed on a tip part 31 of the shaft 3. Further, a contact force sensor 5 is disposed in the shaft 3 at the tip part 31 of the shaft 3.

The deflection member 21 provided on the control handle 2 is a member for deflecting the tip part 31 of the shaft 3. The deflection member 21 deflects the tip part 31 of the shaft 3 in two directions by pulling an operating wire (not shown) disposed in the shaft 3.

A cable 32 and an irrigation tube 33 are derived from the rear of the control handle 2, wherein the cable 32 is connected to a high frequency generator or a controller, and the irrigation tube 33 is connected to a fluid source. The high frequency generator is connected to the tip electrode 4 and supplies high frequency energy to the tip electrode 4. In addition, the controller controls an electrical output signal or input signal and has functions of controlling the state of high frequency power supply to the tip electrode 4 and receiving the output signal from the contact force sensor 5 to measure the contact force.

As shown in FIG. 1 and FIG. 2, the shaft 3 is in an elongated shape and is formed with a lumen 34. The shaft 3 has moderate rigidity and flexibility. In the lumen 34, lead wire insertion tubes 35 and 36 that are hollow are disposed in the longitudinal direction.

A material for forming the shaft 3 may include a synthetic resin such as polyurethanes, polyolefins, polyamides, and polyether polyamides, for example. Moreover, the shaft 3 has an outer diameter of 8 Fr or less and a length dimension in a range of 90 mm to 110 mm.

The tip electrode 4, as shown in FIG. 2, has a bullet shape and is fixed to the tip part 31 of the shaft 3. The tip electrode 4 has a cylindrical recess 41 on the rear end side. The contact force sensor 5 is connected to the recess 41. In addition, an electrode lead wire 42 is connected to at the rear end side of the tip electrode 4. The electrode lead wire 42 is inserted into the lead wire insertion tube 36 and connected to the high frequency generator. That is, the tip electrode 4 is electrically connected to the high frequency generator for supplying the high frequency energy from the high frequency generator to the tip electrode 4.

The tip electrode 4 has an outer diameter of 8 Fr or less, preferably substantially equal to the outer diameter of the shaft 3. A material for forming the tip electrode 4 may include a metallic material having favorable thermal conductivity, such as platinum, gold, stainless steel, and titanium alloy, for example.

A flow path (not shown) is formed in the tip electrode 4 for delivering a fluid, such as a saline solution, conveyed from the irrigation tube 33 to the outside.

Next, details of the contact force sensor 5 are described with reference to FIG. 2 through FIG. 6. To illustrate the wiring of the lead wire derived from the contact force sensor, FIG. 3 provides a plan view with the tip electrode 4 and the shaft 3 of FIG. 2 excluded.

The contact force sensor 5 is fabricated using a silicon semiconductor material by a MEMS (Micro Electro Mechanical System) technique that uses a semiconductor machining process, as described below. The contact force sensor 5 is provided with a sensor configuration 6 and a stress-electricity conversion element 7 formed in the sensor configuration 6.

As shown in FIG. 4 and FIG. 5, the sensor configuration 6 of the present embodiment includes a first sensor configuration 61 and a second sensor configuration 62.

The first sensor configuration 61 includes a base part 611 and a contact force transmission part 612. The base part 611 includes a ring-shaped part 611a and a plurality of arm parts 611b (three, specifically) that extend from an inner wall of the ring-shaped part 611a to a central part.

The contact force transmission part 612 that has a substantially cylindrical shape is formed in the central part of the ring-shaped part 611a. The contact force transmission part 612 is connected with the arm parts 611b and extends in a direction orthogonal to the base part 611. In other words, the plurality of arm parts 611b are formed radially in a radial direction from an outer peripheral wall of the contact force transmission part 612 toward the inner wall of the ring-shaped part 611a.

The stress-electricity conversion element 7, as shown in FIG. 6, is formed in the base part 611 at the rear side of the first sensor configuration 61. FIG. 6 illustrates the rear side of the first sensor configuration 61 in a planar manner.

Although the stress-electricity conversion element 7 is indicated by solid lines for explanatory purposes, the stress-electricity conversion element 7 is in fact integrally built in the base part 611.

The stress-electricity conversion element 7 is a piezoresistive element having a strain gauge function that, when strain is applied, the electric resistance varies due to the displacement. The piezoresistive elements (S1-*a*, S1-*b*), (S2-*a*, S2-*b*), and (S3-*a*, S3-*b*) are disposed on one side (the rear side, specifically) of the arm parts 611*b* respectively at the central side and the outer peripheral side of each arm part 611*b*. In other words, the piezoresistive elements (S1-*a*, S1-*b*), (S2-*a*, S2-*b*), and (S3-*a*, S3-*b*) are arranged in pairs respectively on the arm parts 611*b*. An electrode part 71 is respectively formed at both ends of the piezoresistive elements (S1-*a*, S1-*b*), (S2-*a*, S2-*b*), and (S3-*a*, S3-*b*). The electrode part 71 is electrically connected to the power supply side.

More specifically, a ring-shaped inner wiring pattern 72 is formed at the central part of the rear side of the base part 611, and an outer wiring pattern 73 also being ring-shaped is formed in the ring-shaped part 611*a*. These wiring patterns 72 and 73 are formed of a material that is tin-plated nickel or gold, for example.

The piezoresistive elements (S1-*a*, S1-*b*) are described as a representative example. One electrode 71*a* of the piezoresistive element S1-*a* disposed at the central side is disposed on the inner wiring pattern 72 and connected to the wiring pattern 72. The other electrode 71*b* is disposed on the arm part 611*b*, and a lead wire 74 is connected to the electrode 71*b*.

In addition, one electrode 71*a* of the piezoresistive element S1-*b* disposed at the outer peripheral side is disposed on the arm part 611*b*, and a lead wire 75 is connected to the electrode 71*a*. The other electrode 71*b* is disposed on the outer wiring pattern 73 and connected to the wiring pattern 73. One electrode 71*a* of the piezoresistive element S1-*b* disposed at the outer peripheral side is an insulated electrode that is not electrically connected to the piezoresistive element S1-*b*. However, when the first sensor configuration 61 and the second sensor configuration 62 are combined, as described below, for example, a piezoresistive element S4-*b* formed on the side of the second sensor configuration 62 is connected via the electrode.

The piezoresistive elements (S2-*a*, S2-*b*) and (S3-*a*, S3-*b*) are disposed and connected in the same manner as the piezoresistive elements (S1-*a*, S1-*b*). Further, lead wires 76 and 77 that are led out to the power supply side are connected to the inner wiring pattern 72 and the outer wiring pattern 73. The lead wire 76 may be connected to one electrode 71*a* of the piezoresistive element S1-*a* disposed at the central side, for example. The lead wire 77 may be connected to the other electrode 71*b* of the piezoresistive element S1-*b* disposed at the outer peripheral side.

The connection of the lead wires 74 and 75 to the electrodes 71*b* and 71*a* and the connection of the lead wires 76 and 77 to the wiring patterns 72 and 73, as described above, are performed using soldering by the so-called pulse heat method. The pulse heat method is a soldering method that uses Joule heat generated by applying a pulse current to a tool (heater chip) to locally and instantaneously heat the site to be soldered so as to achieve the connection. Thus, the lead wires 74, 75, 76, and 77 can be connected in a narrow area reliably.

With such wiring relations between the piezoresistive elements (S1-*a*, S1-*b*), (S2-*a*, S2-*b*), and (S3-*a*, S3-*b*), the piezoresistive elements (S1-*a*, S1-*b*), (S2-*a*, S2-*b*), and (S3-*a*, S3-*b*) are all connected to the inner wiring pattern 72 and the outer wiring pattern 73 respectively. Therefore, it is possible to reduce the number of lead wires and simplify the wiring relations.

As shown in FIG. 5, the second sensor configuration 62 is a coupling member to be combined to the rear side of the first sensor configuration 61. The second sensor configuration 62 includes a coupling surface 621 and a cylindrical outer peripheral wall 622.

The coupling surface 621 is formed into a shape that conforms to the shape of the rear side of the first sensor configuration 61. The coupling surface 621 has a ring-shaped part 621*a* at the central part, and a plurality of arm parts 621*b* are formed radially in a radial direction from an outer peripheral wall of the ring-shaped part 621*a* toward the inner peripheral wall of cylindrical outer peripheral wall 622.

Though not specified here, on the coupling surface 621, the piezoresistive elements (S4-*a*, S4-*b*), (S5-*a*, S5-*b*), and (S6-*a*, S6-*b*), i.e. the stress-electricity conversion element 7, are formed in the arm parts 621*b* respectively and ring-shaped inner wiring pattern 78 and outer wiring pattern 79 are formed, in the same manner as the first sensor configuration 61. Lead wires (not shown) are connected to these piezoresistive elements (S4-*a*, S4-*b*), (S5-*a*, S5-*b*), and (S6-*a*, S6-*b*) in the same manner as the first sensor configuration 61.

The first sensor configuration 61 and the second sensor configuration 62 having such structures are combined such that the base part 611 on the rear side of the first sensor configuration 61 faces and fits to the coupling surface 621 of the second sensor configuration 62, so as to form the sensor configuration 6. Specifically, the arm parts 611*b* of the first sensor configuration 61 and the arm parts 621*b* of the second sensor configuration 62 are disposed to face each other. The respective electrodes 71 of the piezoresistive elements (S1-*a*, S1-*b*), (S2-*a*, S2-*b*), and (S3-*a*, S3-*b*) disposed in the base part 611 and the respective electrodes 71 of the piezoresistive elements (S4-*a*, S4-*b*), (S5-*a*, S5-*b*), and (S6-*a*, S6-*b*) disposed on the coupling surface 621 are soldered and coupled to each other.

In a state where the first sensor configuration 61 and the second sensor configuration 62 are combined, as shown in FIG. 4, the piezoresistive elements (S1-*a*, S1-*b*), (S2-*a*, S2-*b*), and (S3-*a*, S3-*b*) formed in the first sensor configuration 61 and the piezoresistive elements (S4-*a*, S4-*b*), (S5-*a*, S5-*b*), and (S6-*a*, S6-*b*) formed in the second sensor configuration 62 face each other respectively. For example, the piezoresistive elements S1-*a* and S4-*a* face each other, and the piezoresistive elements S1-*b* and S4-*b* face each other.

Connection parts of the electrodes 71*b* and 71*a* and the lead wires 74 and 75 in the first sensor configuration 61 and connection parts of the electrodes 71*b* and 71*a* and the lead wires in the second sensor configuration 62 are sandwiched between the base part 611 of the first sensor configuration 61 and the coupling surface 621 of the second sensor configuration 62. Thus, the coupling strength of the connection parts between the electrodes and the lead wires can be improved.

Disposing the contact force sensor 5 into the lumen 34 of the shaft 3 is described with reference to FIG. 2 and FIG. 3 again. As shown in FIG. 2, the contact force sensor 5 is mounted on the inner wall of the shaft 3. In the mounting state, a tip side portion of the contact force transmission part 612 of the contact force sensor 5 is fitted and connected to the recess 41 of the tip electrode 4.

Further, as shown in FIG. 3, the lead wires 74 and 75, which are derived from a joint between the base part 611 of the first sensor configuration 61 and the coupling surface 621 of the second sensor configuration 62 of the contact force sensor 5, are inserted through the lead wire insertion tube 35 and connected to the controller via the control handle 2. Besides, a distribution tube is disposed in the lumen 34 of the shaft 3, wherein the flowing of the fluid conveyed from the irrigation tube 33 is not illustrated in the figure.

Next, the connection state of the stress-electricity conversion element (piezoresistive element) 7 is described with reference to FIG. 7. By combining the first sensor configuration 61 and the second sensor configuration 62 through soldering, the piezoresistive elements (S1-a, S1-b), (S2-a, S2-b), and (S3-a, S3-b) and the piezoresistive elements (S4-a, S4-b), (S5-a, S5-b), and (S6-a, S6-b) are connected to form a bridge circuit.

Specifically, series circuits each connecting one of the pairs of the piezoresistive elements S1-a and S1-b, S2-a and S2-b, S3-a and S3-b, S4-a and S4-b, S5-a and S5-b, and S6-a and S6-b are connected in parallel to the power supply side. Output terminals A, B, C, D, E, and F are respectively connected to connection middle portions between the piezoresistive elements of the series circuits. Output voltages are output from the output terminals A, B, C, D, E, and F when strain is applied to the piezoresistive elements.

Regarding the outline of the production processes of the contact force sensor 5, an example is described below with reference to FIG. 8(a) to FIG. 8(e). The contact force sensor 5 is fabricated using a silicon semiconductor material by the MEMS technology. The present embodiment illustrates a case of fabricating the first sensor configuration 61 and the piezoresistive elements 7.

Figure 8A:
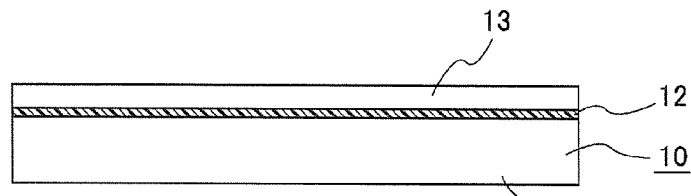
FIG. 8(a) to FIG. 8(e) include cross-sectional views outlining production processes of the contact force sensor.

First, a SOI (silicon on insulator) substrate 10 is used for the production (FIG. 8(a)). The SOI substrate 10 is prepared by forming a silicon oxide film, i.e. an insulating layer 12, on a silicon wafer 11 and then laminating a silicon film 13 thereon.

Figure 8B:
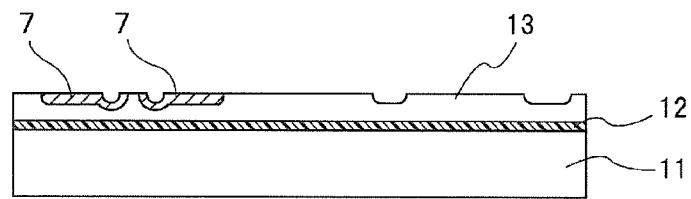

Through previous processes such as a photolithography process or an etching process, the piezoresistive elements 7 are formed (FIG. 8(b)). When the piezoresistive elements 7 are formed, an ion implantation method is applied to implant boron into the silicon film 13. The boron may be diffused into the silicon film 13 by a thermal diffusion method.

Figure 8C:
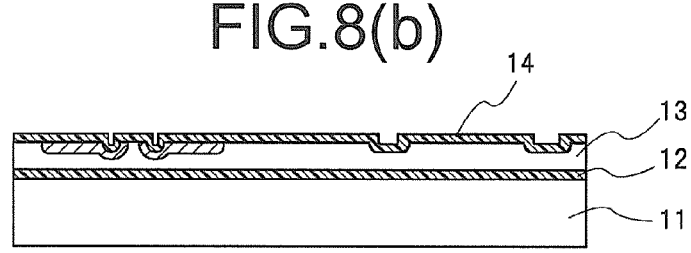
Figure 8D:
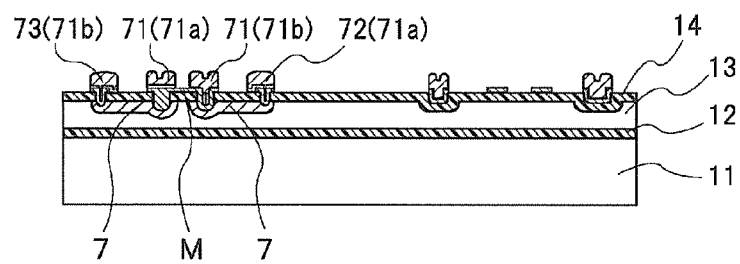
Figure 8E:
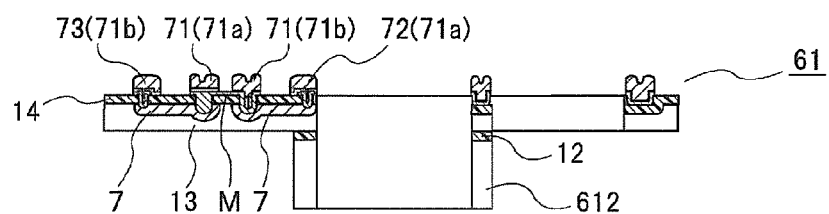

Then, an insulating layer 14 is formed on the silicon film 13 (FIG. 8(c)). For example, the insulating layer 14 that is a silicon oxide film is formed on the silicon film 13 by a plasma chemical vapor deposition (CVD) method.

Subsequently, through a photolithography process or an etching process, a film M is deposited by a sputtering method using a metal material, such as aluminum or aluminum alloy, to connect the piezoresistive elements 7. Thereafter, the inner wiring pattern 72 and the outer wiring pattern 73 are formed to include the electrodes 71 and connect to the piezoresistive elements 7 (FIG. 8(d)). The inner wiring pattern 72, the outer wiring pattern 73, and the electrodes 71 are formed, for example, by depositing a film by a sputtering method using a metal material such as nickel or gold, patterning the film, and applying a tin plating thereon. The tin plating may be omitted. In addition, it is preferable to form an insulating layer by laminating a silicon nitride film on the deposited film M of the metal material.

Next, the upper and lower surfaces of the silicon wafer 11 as illustrated are etched by DRIE (Deep Reactive Ion Etching), for example, and the insulating layer 12, i.e. the unnecessary silicon oxide film, is removed by etching, so as to form the contact force transmission part 612. Afterward, a photoresist not shown in the figure is stripped by using a stripping solution to form a predetermined form of the first sensor configuration 61 (FIG. 8(e)). In this case, because the insulating layer 12 is left to intervene between the contact force transmission part 612 and the base part 611, the insulation between the contact force transmission part 612 and the base part 611 can be ensured.

The first sensor configuration 61 and the piezoresistive elements 7 are fabricated by the foregoing processes. Accordingly, the piezoresistive elements 7 are formed to be integrally built in the base part 611 of the first sensor configuration 61. Though not specified here, the second sensor configuration 62 can also be fabricated by the same processes as the aforementioned first sensor configuration 61.

Hereinafter, a method of an ablation treatment using the aforementioned catheter 1 is described. The ablation treatment identifies the abnormal site of the heart by pre-mapping and then cauterizes the abnormal site of the inner wall tissue of the heart to coagulate and necrose the abnormal site.

When using the catheter 1 to cauterize the abnormal site, the catheter 1 is mainly inserted from the femoral vein or femoral artery at the groin and the tip of the catheter 1 is visualized by radiography and directed to reach the heart. The control handle 2 is operated to make the tip electrode 4 of the catheter 1 in contact with the abnormal site of the inner wall tissue of the heart, and a high frequency current, e.g. 13.56 MHz, is applied from the high frequency generator to between the tip electrode 4 and a counter electrode plate positioned on the back of the patient to cauterize the abnormal site.

In this case, since the catheter 1 is provided with the contact force sensor 5, it is possible to detect the contact force (stress) of the tip electrode 4 in contact with the inner wall tissue of the heart. Specifically, the stress-electricity conversion element 7 (the piezoresistive element) formed in the contact force sensor 5 reacts to small strain, and when strain is applied, the electrical resistance changes.

When the contact force is applied to the tip electrode 4, the contact force is transmitted to the sensor configuration 6. First, the contact force is transmitted to the contact force transmission part 612 of the first sensor configuration 61, and then transmitted from the contact force transmission part 612 to the arm parts 611b of the base part 611. The contact force is also transmitted to the arm parts 621b of the coupling surface 621 of the second sensor configuration 62 at the same time.

Therefore, the contact force is directly applied to the stress-electricity conversion element 7 (the piezoresistive element) formed in the arm parts 611b and the arm parts 621b, and the stress-electricity conversion element 7 (the piezoresistive element) senses three-dimensionally the compressive/stretching strain.

For example, in a case where the stress is applied from a certain direction to the arm part 611b and the arm part 621b formed with the piezoresistive elements (S1-a, S1-b) and (S4-a, S4-b) through the contact force transmission part 612, as the piezoresistive element S1-a is compressed and the resistance value decreases, the piezoresistive element S1-b is stretched and resistance value increases. On the other hand, the piezoresistive element S4-a is stretched and the resistance value increases, and the piezoresistive element S4-b is compressed and the resistance value decreases.

Accordingly, a differential output of the output voltages of the output terminal A and the output terminal D shown in FIG. 7 can be detected by the controller to measure the contact force.

In this manner, the contact force can be detected three-dimensionally based on the differential output of the output voltages of the output terminal A and the output terminal D, the differential output of the output voltages of the output terminal B and the output terminal E, and the differential output of the output voltages of the output terminal C and the output terminal F.

According to the present embodiment as described above, because the stress-electricity conversion element 7 (the piezoresistive element) is formed to be integrally built in the sensor configuration 6, the contact force is directly applied to the stress-electricity conversion element 7 (the piezoresistive element), the contact force of the tip electrode 4 can be detected with high sensitivity and high accuracy, and the ablation treatment can be performed with a proper contact force.

The invention is not limited to the configuration of the aforementioned embodiment. Various modifications may be made without departing from the spirit of the invention. In addition, the aforementioned embodiment is disclosed as one example and is not intended to limit the scope of the invention.

In the aforementioned embodiment, the sensor configuration is composed of the first sensor configuration and the second sensor configuration, for example. However, the sensor configuration may include only the first sensor configuration without the second sensor configuration.

What is claimed is:

1. A contact force sensor fabricated by machining a semiconductor material, the contact force sensor comprising:
   a first sensor configuration comprising a base part, a contact force transmission part formed in a direction orthogonal to the base part, and a first stress-electricity conversion element formed on a rear side of a forming surface of the base part, wherein the contact force transmission part is formed on the forming surface of the base part and the first stress-electricity conversion element converts a displacement of the contact force transmission part to an electrical signal; and
   a second sensor configuration comprising a coupling surface coupled to a rear side of the first sensor configuration, and a second stress-electricity conversion element being formed on the coupling surface,
   wherein the rear side of the first sensor configuration and the coupling surface of the second sensor configuration are coupled to sandwich a connection part of a first lead wire connected to the first stress-electricity conversion element and a connection part of a second lead wire connected to the second stress-electricity conversion element, and are arranged such that the first stress-electricity conversion element and the second stress-electricity conversion element formed respectively face each other.

2. The contact force sensor according to claim 1, wherein the base part of the first sensor configuration comprises a ring-shaped part and a plurality of arm parts extending from an inner side of the ring-shaped part to a central part, and the contact force transmission part is connected with the plurality of arm parts at the central part of the ring-shaped part.

3. The contact force sensor according to claim 2, wherein at least one first stress-electricity conversion element is formed respectively in the plurality of arm parts.

4. The contact force sensor according to claim 3, wherein a wiring pattern connecting a plurality of the first stress-electricity conversion elements together is formed in the base part of the first sensor configuration.

5. The contact force sensor according to claim 1, wherein an insulating layer is interposed between the base part and the contact force transmission part.

6. The contact force sensor according to claim 5, wherein the semiconductor material is a silicon on insulator substrate.

7. The contact force sensor according to claim 1, wherein the connection part of the first lead wire connected to the first stress-electricity conversion element is coupled with the connection part of the second lead wire connected to the second stress-electricity conversion element by soldering and sandwiched between the first sensor configuration and the second sensor configuration.

8. The contact force sensor according to claim 1, wherein the coupling surface of the second sensor configuration is formed into a shape suitable to a shape of the rear side of the first sensor configuration.

9. The contact force sensor according to claim 1, wherein the first stress-electricity conversion element and the second stress-electricity conversion element form a bridge circuit, and all the first stress-electricity conversion elements and the second stress-electricity conversion elements that form the bridge circuit detect the displacement of the contact force transmission part.

10. The contact force sensor according to claim 2, wherein the coupling surface of the second sensor configuration is formed into a shape suitable to a shape of the rear side of the first sensor configuration.

* * * * *